United States Patent [19]

Panicali et al.

[11] Patent Number: 5,656,465
[45] Date of Patent: Aug. 12, 1997

[54] METHODS OF IN VIVO GENE DELIVERY

[75] Inventors: Dennis L. Panicali, Acton, Mass.;
Steven A. Rosenberg, Bethesda, Md.;
Linda R. Gritz, Somerville, Mass.

[73] Assignee: Therion Biologics Corporation, Cambridge, Mass.

[21] Appl. No.: 238,611

[22] Filed: May 4, 1994

[51] Int. Cl.$^6$ .................................................. C12N 15/00
[52] U.S. Cl. ............................. 435/172.3; 435/320.1; 935/23; 935/32; 935/55; 935/57; 935/70; 935/71
[58] Field of Search .......................... 514/44; 424/93.21; 435/172.3

[56] References Cited

FOREIGN PATENT DOCUMENTS

WO94/04196  3/1994  WIPO .

OTHER PUBLICATIONS

Marshall, E. Science 269: 1050–1054, 1995.
Rosenberg et al. NEJM 323:570, 1990.
Jenkins et al. AIDS Res & Human Retroviruses 7: 991, 1991.
Feller et al. Virology 183: 578, 1991.
Taylor et al. Vaccine 6: 497, 1988.
Ramshaw et al. Immunological Reviews 127: 157, 1992.
Binns, et al., "Comparison of a Conserved Region in Fowlpox Virus and Vaccinia Virus Genomes and the Translocation of the Fowlpox Virus", *J. Gen. Virol.*, 69: 1275–1283 (1988).
Boursnell, et al., "Insertion of the fusion gene from Newcastle disease virus into a non–essential region in the terminal repeats of fowlpox virus and demonstration of protective immunity induced by the recombinant", *Journal of General Virology*, 71:621–628 (1990).
Boyle, et al., "Fowlpox Virus Thymidine Kinase: Nucleotide Sequence and Relationships to Other Thymidine Kinases", *Virology*, 156:355–365 (1987).
Calvert, et al., "Fowlpox Virus Recombinants Expressing the Envelope Glycoprotein of an Avian Reticuloendotheliosis Retrovirus Induce Neutralizing Antibodies and Reduce Viremia in Chickens", *Journal of Virology*, 67:3069–3076 (1993).
Cepko, et al., "Construction and Applications of a Highly Transmissible Murine Retrovirus Shuttle Vector", *Cell*, 37:1053–1062 (1984).
Culliton, B.J., "Fighting Cancer with Designer Cells", *Science*, 244:1430–1433 (1989).
Culver, et al., "In Vivo Gene Transfer with Retroviral Vector–Producer Cells for Treatment of Experimental Brain Tumors", *Science*, 256:1550–1552 (1992).
Falkner, et al., "*Escherichia coli gpt* Gene Provides Dominant Selection for Vaccinia Virus Open Reading Frame Expression Vectors", *Journal of Virology*, 62:1849–1854 (1988).
Feller, et al., "Isolation and Molecular Characterization of the Swinepox Virus Thymidine Kinase Gene", *Virology*, 183:578–585 (1991).

Franke, et al., "Neomycin Resistance as a Dominant Selectable Marker for Selection and Isolation of Vaccinia Virus Recombinants", *Molecular and Cellular Biology*, 5:1918–1924 (1985).
Hruby, et al., "Fine structure analysis and nucleotide sequence of the vaccinia virus thymidine kinase gene", *Proc. Natl. Acad. Sci. USA*, 80:3411–3415 (1983).
Jenkins, et al., "Formation of Lentivirus Particles by Mammalian Cells Infected with Recombinant Fowlpox Virus", *Aids Research and Human Retroviruses*, 7:991–998 (1991).
Kasid, et al., "Human gene transfer: Characterization of human tumor–infiltrating lymphocytes as vehicles for retroviral–mediated gene transfer in man", *Proc. Natl. Acad. Sci. USA*, 87:473–477 (1990).
Lowe, et al., "Varicella–zoster virus as a live vector for the expression of foreign genes", *Proc. Natl. Acad. Sci. USA*, 84:3896–3900 (1987).
Lytvyn, et al., "Comparison of the thymidine kinase genes from three entomopoxviruses", *Journal of General Virology*, 73:3235–3240 (1992).
Mackett, et al., "Vaccinia virus: A selectable eukaryotic cloning and expression vector", *Proc. Natl. Acad. Sci. USA*, 79:7415–7419 (1982).
Morin, et al., "Recombinant adenovirus induces antibody response to hepatitus B virus surface antigen in hamsters", *Proc. Natl. Acad. Sci. USA*, 84:4626–4630 (1987).
Mukhopadhyay, et al., "Specific Inhibition of K–ras Expression and Tumorigenicity of Lung Cancer Cells by Antisense RNA$^1$", *Cancer Research*, 51:1744–1748 (1991).
Muul, et al., "Identification of Specific Cytolytic Immune Responses Against Autologous Tumor In Humans Bearing Malignant Melanoma", *The Journal of Immunology*, 138:989–995 (1987).
Panicali, et al., "Vaccinia virus vectors utilizing the β–galactosidase assay for rapid selection of recombinant viruses and measurement of gene expression", *Gene*, 47:193–199 (1986).
Panicali, et al., "Construction of poxviruses as cloning vectors: Insertion of the thymidine kinase gene from herpes simplex virus into the DNA of infectious vaccinia virus", *Proc. Natl. Acad. Sci. USA*, 79:4927–4931 (1982).

(List continued on next page.)

*Primary Examiner*—Suzanne E. Ziska
*Attorney, Agent, or Firm*—Sewall P. Bronstein; Ronald I. Eisenstein; David S. Resnick

[57] ABSTRACT

We have discovered that using non-integrative viral vectors having low replicative efficiency for insertion of a gene into a cell such as a lymphocyte or a tumor cell is a preferred system for transforming such cells for use in somatic cell therapy or gene therapy. These vectors are preferably cytoplasmic viral vectors, as opposed to nuclear viral vectors. Preferred cytoplasmic vectors include DNA viruses such as pox viruses and iridoviruses and RNA viruses such as picornavirus, calicivirus and togavirus. More preferably the virus used will not be capable of sustained replication in the target cell. For example, a preferred pox virus for human cells will be an avipox, or suipox in contrast to an orthopox virus such as vaccinia.

26 Claims, No Drawings

OTHER PUBLICATIONS

Hwu, et al., "Functional and Molecular Characterization of Tumor–Infiltrating Lymphocytes Transduced with Tumor Necrosis Factor–α cDNA for the Gene Therapy of Cancer in Humans", *The Journal of Immunology*, 150:4104–4115 (1993).

Hwu, et al., "Lysis of Ovarian Cancer Cells by Human Lymphocytes Redirected with a Chimeric Gene Composed of an Antibody Variable Region and the Fc Receptor Y Chain", *The Journal of Experimental Medicine*, 178:361–366 (1993).

Pardoll, D. M., "Cancer vaccines", *Immunology Today*, 14:310–316 (1993).

Podda, et al., "Transfer and expression of the human multiple drug resistance gene into live mice", *Proc. Natl. Acad. Sci. USA*, 89:9676–9680 (1992).

Ramishaw, et al., "Expression of Cytokines by Recombinant Vaccinia Viruses: A Model for Studying Cytokines in Virus Infections in vivo", *Immunological Reviews*, No. 127, pp. 157–182 (1992).

Rosel, et al., "Conserved TAAATG Sequence at the Transcriptional and Translational Initiation Sites of Vaccinia Virus Late Genes Deduced by Structural and Functional Analysis of the HindIII H Genome Fragment", *Journal of Virology*, 60:436–449 (1986).

Rosenberg, et al., "Gene Transfer Into Humans—Immunotherapy of Patients With Advanced Melanoma, Using Tumor–Infiltrating Lymphocytes Modified By Retroviral Gene Transduction", *The New England Journal of Medicine*, 323:570–578 (1990).

Rosenberg, et al., "Use of Tumor–Infiltrating Lymphocytes and Interleukin–2 In The Immunotherapy of Patients With Metastatic Melanoma", *The New England Journal of Medicine*, 319:1676–1680 (1988).

Sorrentino, et al., "Selection of Drug–Resistant Bone Marrow Cells in Vivo After Retroviral Transfer of Human MDR1", *Science*, 257:99–102 (1992).

Spehner, et al., "Construction of Fowlpox Virus Vectors with Intergenic Insertions: Expression of the β–Galactosidase Gene and the Measles Virus Fusion Gene", *Journal of Virology*, 64:527–533 (1990).

Spyropoulos, et al., "Delineation of the Viral Products of Recombination in Vaccinia Virus–Infected Cells", *Journal of Virology*, 62:1046–1054 (1988).

Tao, et al., "Idiotype/granulocyte–macrophage colony––stimulating factor fusion protein as a vaccine for B–cell lymphoma", *Nature*, 362:755–758 (1993).

Taylor, et al., "Recombinant fowlpox virus inducing protective immunity in non–avian species", *Vaccine*, 6:497–503 (1988).

Topalian, et al., "Tumor–Specific Cytolysis By Lymphocytes Infiltrating Human Melanomas", *The Journal of Immunology*, 142:3714–3725 (1989).

Upton, et al., "Identification and Nucleotide Sequence of the Thymidine Kinase Gene of Shope Fibroma Virus", Journal of Virology, 60:920–927 (1986).

Weir, et al., "Nucleotide Sequence of the Vaccinia Virus Thymidine Kinase Gene and the Nature of Spontaneous Frameshift Mutations", Journal of Virology, 46:530–537 (1983).

METHODS OF IN VIVO GENE DELIVERY

The present invention is directed to a method of in vivo and ex vivo gene delivery, for a variety of cells where permanent transformation is not necessary.

In recent years, substantial attention has been given to the promise of in vivo gene therapy. This term has been used to describe a wide variety of methods using recombinant biotechnology techniques to deliver a variety of different materials to a cell. Such methods include, for example, the delivery of a gene, antisense RNA, a cytotoxic agent, etc., by a vector to a mammalian cell, preferably a human cell either in vivo or ex vivo. Most of the initial work has focused on the use of retroviral vectors to transform these cells. This focus has resulted from the ability of retroviruses to infect cells and have their genetic material integrated into the host cell with high efficiency. The retroviral vector is typically a modified Moloney Murine Leukemia Virus (MMLV) which has had its packaging sequences deleted to prevent packaging of the entire retroviral genome.

However, numerous difficulties with retroviruses have been reported. For example, problems have been encountered in infecting certain cells. Retroviruses typically enter cells through receptors and if such receptors are not present on the cell, or not present in large numbers, then infection is not possible or efficient. These viruses are also relatively labile in comparison to other viruses. Outbreaks of wild-type virus from recombinant virus-producing cell lines have also been reported with the vector itself causing a disease. Moreover, these viruses only express in dividing cells.

In addition, retroviral-mediated gene transfer methods typically result in stable transformation of target cells. Although this is often regarded as advantageous, the stable transformation of a patient's somatic cells makes it difficult to reverse the treatment regimen if undesirable side effects dictate that it should be stopped. Moreover, there is always the concern that genetic transformation might lead to malignant transformation of the cell.

Other viruses have been proposed as vectors such as adenovirus, adeno-associated virus (AAV), herpes virus, vaccinia virus, etc. In addition, various non-viral vectors such as ligand-DNA-conjugates have been proposed. Nevertheless, these vectors all pose certain problems. For example, the vector itself must not become a potential source for infection to the individual treated. However, as discussed above, outbreaks of wild-type retroviruses have been reported in some cell lines. Similarly, the use of herpes virus as a vector has been found to result in persistence of the virus. The use of vaccinia virus as a vector has proven fatal to immuno-compromised individuals. Such individuals constitute one major target of gene therapy. Furthermore, many of these vectors can contain and express only a relatively small amount of genetic material. This is undesirable for numerous situations in which the ability to express multiple products is preferred. Accordingly, it would be useful to have a vector system that will be able to infect cells, efficiently carry and express a large amount of genetic material and not be cytotoxic to the cell.

SUMMARY OF INVENTION

We have discovered that using non-integrative viral vectors having low replicative efficiency for insertion of a gene into a cell such as a lymphocyte or a tumor cell is a preferred system for transforming such cells for use in somatic cell therapy or gene therapy. These vectors are preferably cytoplasmic viral vectors, as opposed to nuclear viral vectors. Preferred cytoplasmic vectors include DNA viruses such as pox viruses and iridoviruses and RNA viruses such as picornavirus, calicivirus and togavirus. More preferably the virus used will not be capable of sustained replication in the target cell. For example, a preferred pox virus for human cells will be an avipox, or suipox.

The gene (or genes) to be inserted into the target cells are inserted into the vector by standard means, such as homologous recombination or use of a unique insertion site. The vector is then introduced into the target cells by any known method.

The transformed cell can be used for somatic cell therapy or in vivo gene therapy. The vector system used will not integrate into the target's chromosomes, and will not result in sustained replication and infection of other cells.

Therefore, the risks of long term exposure, either from the viral vector or the added gene, is substantially reduced.

DETAILED DESCRIPTION OF THE INVENTION

We have now discovered that using a non-integrating virus, preferably a cytoplasmic virus, is a preferred vector for delivery of genetic material. The genetic material (genes) carried by these vectors will thus not be present in the nucleus of the target cell, unless specifically desired. The vector preferably has a low replicative efficiency in the target cell.

It was traditionally believed that gene delivery vectors should be modified versions of infective nuclear viruses, such as retroviruses and herpes virus. However, we have discovered that these type of vectors are not desirable for many purposes. This is particularly true where you are interested in a short-term delivery of a gene product (e.g., tumor necrosis factor (TNF), B7-1, B7-2 and granulocyte macrophage colony stimulating factor (GM-CSF) whose long-term expression is not only unnecessary but can pose a risk for the host. Similarly, certain viral vectors are so potent that they overwhelm the host cell and prove lethal to it in 24 to 48 hours. Thus, the viral vector used, will be based upon a virus that is non-lytic to the target cell in a 48 hour time span, more preferably a 96 hour time span, and still more preferably, a 120 hour or longer time span. As the term is used herein a non-lytic, virus is one that will not kill most target cells in the host animal or a tissue culture in a short period of time during which the viable infected cells will be expressing the gene product. For example, it preferably will not kill more than about 25% of the target cells it is being used in within 48 hours, more preferably 72 hours, still more preferably, 96 hours. More preferably, it will not kill more than about 10% of the target cells in the host animal or tissue culture it is used in within 48 hours, more preferably 72 hours, and still more preferably 96 hours. Even more preferably, such a transformed target cell population will be expressing the delivered gene product for a period of 1 to 2 weeks after initial infection. This can readily be determined by assaying samples of the target cell for viability, e.g., by staining with trypan blue, and gene expression, e.g., measuring protein production with ELISA.

The term "short-term" delivery system described herein is preferably directed to the use of vector systems that although capable of expressing the desired genetic material for at least about 1 week will result in the transient expression of the gene product. Preferably, the expression will be for less than about 2 months, more preferably, less than about 1 month. In addition, by using an avirulent virus for the selected animal host the virus will not cause disease in the host. If any adverse effects are observed, such effects can be further curtailed as described below. Moreover, the delivery system described herein is capable of "controlled release" of a desired protein by continuously expressing specific amounts of the desired protein over a given period of time.

A non-integrating virus is one whose DNA will not be integrated into the host cell's chromosomes. However, as will be discussed below, it is possible in certain instances where integration of the gene (or genes) is desired to design the vectors so that it will have gene(s) that can be integrated into the nucleic acid of the host cell such as incorporating an "integration" system into the vector. For example, adeno-associated virus (AAV) integrates at a specific location in a host cell chromosome. Recombinant AAV containing foreign genes have been constructed. The recombinant AAV genome could be incorporated into a viral vector genome (e.g., suipoxvirus). The viral vector could deliver the AAV to the host cell and the AAV could integrate the recombinant DNA into the host genome.

Preferred non-integrating viruses are cytoplasmic viruses. These include both DNA and RNA viruses. DNA viruses includes poxviruses such as suipox (e.g. swine pox) capripox, leporipox, avipox (e.g. fowl pox, canary pox) and orthopox (e.g. ectomelia, rabbit pox). Other DNA viruses include iridoviruses such as various insect and frog viruses.

RNA viruses include picornaviruses, caliciviruses, togaviruses, rhaboviruses and coronaviruses. Picornaviruses include enterovirus, cardiovirus, rhinovirus, apthovirus, and hepatitis A. Calicivirus include vesicular exanthema virus of swine, dogs or mink, feline calicivirus and caliciviruses of calves, swine, dogs, fowl and chimps. Togaviruses include bovine viral diarrhea virus, hog cholera, and border disease of sheep. Rhabdoviruses include vesiculoviruses such as vesicular stomatitis virus and Lyssaviruses such as rabies. Coronaviruses include infectious bronchitis virus of fowl, transmissible gastroenteritis virus of swine, hemagglutinin encephalyomyelitis virus of swine, turkey, bluecomb virus, calf coronavirus and feline infectious peritonitis virus.

DNA viruses are preferred for use as vectors. Pox viruses are more preferred for use as vectors.

For example, pox viruses are well known cytoplasmic viruses. Thus, genetic material expressed by such viral vectors typically remain in the cytoplasm and do not have the potential for inadvertent integration of the genetic material carried into host cell genes, unless specific steps are taken such as described above. Furthermore, because these vectors have a large genome, they can readily be used to deliver a wide range of genetic material including multiple genes (i.e., act as a multivalent vector).

The viral vector preferably has a low replicative efficiency in the target cell. This preferably means that no more than about 1 progeny per cell are produced, still more preferably, no more than 0.1 progeny per cell. Replication efficiency can readily be determined empirically by determining the virus titer after infection of the target cell.

As a result of the low replication efficiency and the non-integrative, cytoplasmic nature of the vector, the vector system will not result in sustained replication and infection of other cells. Thus, the vector and transformed cells will not adversely affect cells in the host animal at locations distant from where the target cell is.

The gene delivery system described herein can be used for any host. Preferably, the host will be a mammal or a bird. Preferred mammals include primates such as humans and chimpanzees, domestic animals such as horses, cows, pigs, etc. and pets such as dogs and cats. More preferably, the host animal is a primate or domestic animal. Still more preferably the host animal is a primate such as humans.

In order to further insure that the viral vector used for a particular host animal is avirulent in that animal, in addition to the above criteria, one can readily screen for a viral vector by looking at the virus's host range and tissue specificity. For example, one method is looking at a virus' natural host range. Preferably, the virus vector selected would be from a virus whose primary range of infection is for a different host animal than the animal that the gene delivery system is to be used in. For example, swinepox can be used as a viral vector when the host is a primate such as a human. However, for veterinary purposes where the host is a pig it would not be preferable. Certain highly attenuated or modified strains such as modified orthopox virus (e.g. the MVA strain of vaccinia or strains genetically modified or selected to be non-virulent in their normal host range or in a desired host cell) that are not virulent in their normal host range can, however, be used. Tissue specificity also can be used to preliminarily screen for infectivity and replication efficiency. Specific screening tests are shown in the examples and discussed infra.

Where the host is human, preferred vectors include pox vectors, for example, suipox, such as swinepox, avipox such as fowlpox, canary pox, or pigeon pox, and capripoxvirus. In addition, iridoviruses such as frog virus, and African swine fever virus are also preferred.

This method of delivery can be used in a wide variety of therapies such as somatic cell therapy and in vivo gene gene therapy. For example, it can be used in tumor infiltrating lymphocytes (TIL) therapy, tracheal endothelium or liver cell to correct genetic defects or provide new functions to cells, etc. In tumor infiltrating lymphocytes (TIL) therapy, the host cell used is a lymphocyte subpopulation that targets tumors. Preferably, the host cell used is a human TIL cell. These cells are particularly susceptible to ex vivo gene delivery (sometimes referred to as somatic cell therapy). Further, the genes to be delivered would be those that will enhance the ability of such cells to target and fight the tumor such as TNF, cytokines such as interleukin (IL) (e.g., IL-2, IL-4, IL-10, IL-12), interferons (IFN) (e.g., IFN-γ), Granulocyte macrophage colony stimulating factor (GM-CSF) and co-stimulatory factor (e.g., B7). Preferably, one would use a multivalent vector to deliver, for example, both TNF and IL-2 simultaneously.

Because one of the desired hosts for in vivo gene delivery is humans certain test models have been developed and accepted by the field to determine the efficacy and utility of a vector system. This involves in vitro testing, ex vivo testing and use of marker genes. Thus, susceptibility of a cell to infection and gene expression by a viral vector is typically determined by assays for a reporter gene. A marker gene such as those encoding β-galactosidase (β-gal), chloramphenicol acetyl transferase (CAT), etc. are used for convenience to determine whether a protein can be expressed by that vector in that cell, the quantity and the duration of expression because it is easier to assay for their presence. However, these marker genes are generally accepted as representative of whether any similarly-sized heterologous protein will also be expressed in such cell. This use of marker genes, for example neomycin, to determine efficacy of gene delivery vehicles has been used before human testing with the desired gene. Thus, the skilled artisan based upon this disclosure can readily determine the efficacy of a particular vector in a particular target tissue and host.

We have demonstrated that both fowlpox vectors and swinepox vectors will infect a wide range of human cells of interest including TIL and malignant cells and transiently express heterologous genes without proving rapidly cytopathic to such cell. In addition these vectors can infect and express the heterologous genes in cells at rest.

Any non-integrative viral vector derived from viruses that can express a desired gene in eukaryotic cells without resulting in rapid cell death in that host system can preferably be used. The gene to be delivered is inserted into the vector, which is then introduced into the target host cells by any means known to those of the skill in the art. The viral vectors described herein have low replication efficiency, and more preferably are non-replicating or result in limited productive replication (i.e. less than 15% of the virus will produce infectious progeny, more preferably less than 10%, still more preferably less than 5%, even more preferably less than 1%). Accordingly, there is little, if any, infectious progeny, and the "infection" is self limiting. The viral vector will not spread throughout the neighboring tissue. Therefore, the risks of long term exposure to the expressed protein is reduced.

If additional exposure to the expressed protein is necessary, the desired gene can be reintroduced into the target cells.

Preferred viral vectors for use with human cells are non-lytic, avirulent pox viruses such as avipox [Taylor, et al., *Vaccine*, 6:497–503 (1985) and Jenkins, et al., *AIDS Research And Human Retroviruses* 7:991–998 (1991)] and suipox [Feller, et al., *Virology* 183:578–585 (1991)].

The genetic material that is delivered to the target TIL cell using the method of the present invention may be genes, for example, those that encode a variety of proteins including anticancer and antiviral agents. Such genes include those encoding various hormones, growth factors, enzymes, cytokines, receptors, MHC molecules and the like. The term "genes" includes nucleic acid sequences both exogenous and endogenous to cells into which the virus vector, for example, a pox virus such as swine pox containing the human TNF gene may be introduced. Of particular interest for use as genes for delivery are those genes encoding polypeptides either absent, produced in diminished quantities, or produced in mutant form in individuals suffering from a genetic disease, such as a tumor suppressor gene product such as the retinoblastoma gene product, Wilm's Tumor gene product, adenosine deaminase (ADA) or immunoglobulin. Additionally, it is of interest to use genes encoding polypeptides for secretion from the target cell so as to provide for a systemic effect by the protein encoded by the gene. Specific genes of interest include those encoding TNF, TGF-α, TGF-β, hemoglobin, interleukin-1, interleukin-2, interleukin-3, interleukin-4, interleukin-5, interleukin-6, interleukin-7, interleukin-8, interleukin-9, interleukin-10, interleukin-11, interleukin-12 etc., GM-CSF, G-CSF, M-CSF, human growth factor, co-stimulatory factor B7, insulin, factor VIII, factor IX, PDGF, EGF, NGF, IL-ira, EPO, β-globin and the like, as well as biologically active muteins of these proteins. Genes for insertion into the viral vectors may be from a variety of species; however, preferred species sources for genes of interest are those species into which the viral vector containing the gene of interest is to be inserted. The gene may further encode a product that regulates expression of another gene product or blocks one or more steps in a biological pathway, such as the sepsis pathway. In addition, the gene may encode a toxin fused to a polypeptide, e.g., a receptor ligand, or an antibody that directs the toxin to a target, such as a tumor cell or a virus. Similarly, the gene may encode a therapeutic protein fused to a targeting polypeptide, to deliver a therapeutic effect to a diseased tissue or organ.

The gene may also encode a marker, such as β-galactosidase, CAT, neomycin or methotrexate resistance, whereby the target cells may be selected or detected. The use of such a marker allows the skilled artisan to screen various viral vectors for those that are non-lytic or non-cytopathic in a particular target host cell. (See, Reference Example 2.) For example, the gene encoding β-galactosidase (lacZ) can be inserted into a viral vector, the modified virus vector is then introduced into the target host cell and the production of β-galactosidase is measured. Expression of β-gal provides an indication of viral infectivity and gene expression. Example 3 shows how cytopathic effect can be screened. Example 4 shows how replicative efficiency can be screened.

The basic technique of inserting genes into viruses are known to the skilled artisan and involve, for example, recombination between the viral DNA sequences flanking a gene in a donor plasmid and homologous sequences present in the parental virus (Mackett, et al., *Proc. Natl. Acad. Sci. USA* 79:7415–7419 (1982)). For example, a recombinant virus such as a poxvirus for use in delivering the gene can be constructed in two steps known in the art and analogous to the methods for creating synthetic recombinants of the fowlpox virus described in U.S. Pat. No. 5,093,258, the disclosure of which is incorporated herein by reference. Other techniques include using a unique restriction endonuclease site that is naturally present or artificially inserted in the parental viral vector.

First, the DNA gene sequence to be inserted into the virus can be placed into a plasmid, e.g., an *E. coli* plasmid construct, into which DNA homologous to a section of DNA such as that of the poxvirus has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA which is the desired insertion region. The resulting plasmid construct is then amplified by growth within *E. coli* bacteria and isolated. Preferably, the plasmid also contains an origin of replication such as the *E. coli* origin of replication, and a marker such as an antibiotic resistance gene for selection and propagation in *E. coli*.

Second, the isolated plasmid containing the DNA gene sequence to be inserted is transfected into a cell culture, e.g., chick embryo fibroblasts, along with the poxvirus. Recombination between homologous pox DNA in the plasmid and the viral genome respectively results in a poxvirus modified by the presence of the promoter-gene construct in its genome, at a site which does not affect virus viability.

As noted above, the gene is inserted into a region (insertion region), in the virus which does not affect virus viability of the resultant recombinant virus. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase gene. For example, it has been found in all pox virus genomes examined [leporipoxvirus: Upton, et al., *J. Virology*, 60:920 (1986) (shope fibroma virus); capripoxvirus: Gershon, et al., *J. Gen. Virol.*, 70:525 (1989) (Kenya sheep-1); orthopoxvirus: Weir, et al., *J. Virol.*, 46:530 (1983) (vaccinia); Esposito, et al., *Virology*, 135:561 (1984) (monkeypox and variola virus); Hruby, et al., *PNAS*, 80:3411 (1983) (vaccinia); Kilpatrick, et al., *Virology*, 143:399 (1985)(Yaba monkey tumor virus); avipoxvirus: Binns, et al., *J. Gen. Virol.* 69:1275 (1988) (fowlpox); Boyle, et al., *Virology*, 156:355 (1987) (fowlpox); Schnitzlein, et al., *J. Virological Methods*, 20:341 (1988) (fowlpox, quailpox); entomopox (Lytvyn, et al., *J. Gen. Virol.* 73:3235–3240 (1992))].

In fowlpox, in addition to the TK region, other insertion regions include, for example, BamHI J [Jenkins, et al., *AIDS Research and Human Retroviruses* 7:991–998 (1991)] the EcoRI-HindIII fragment, BamHI fragment, EcoRV-HindIII fragment, BamHI fragment and the HindIII fragment set forth in EPO Application No. 0 308 220 A1. [Calvert, et al., *J. of Virol.* 67:3069–3076 (1993); Taylor, et al., *Vaccine* 6:497–503 (1988); Spehner, et al., (1990) and Boursnell, et al., *J. of Gen. Virol.* 71:621–628 (1990)].

In swinepox preferred insertion sites include the thymidine kinase gene region.

In addition to the requirement that the gene be inserted into an insertion region, successful expression of the inserted gene by the modified poxvirus requires the presence of a promoter operably linked to the desired gene, i.e., in the proper relationship to the inserted gene. The promoter must be placed so that it is located upstream from the gene to be expressed. Promoters are well known in the art and can readily be selected depending on the host and the cell type you wish to target. For example in poxviruses, poxviral promoters should be used, such as the vaccinia 7.5K, 40K, fowlpox. Enhancer elements can also be used in combination to increase the level of expression. Furthermore, the use of inducible promoters, which are also well known in the art, in some embodiments are preferred.

For example, it is possible to make a construct in which the promoter is modulated by an external factor or cue, and in turn to control the level of polypeptide being produced by the vectors by activating that external factor or cue. For example, heat shock proteins are proteins encoded by genes in which the promoter is regulated by temperature. The promoter of the gene which encodes the metal-containing protein metallothionine is responsive to $Cd^+$ ions. Incorporation of this promoter or another promoter influenced by external cues also make it possible to regulate the production of the proteins.

The method of the present invention as mentioned above is useful for delivery of multiple genes to the target host cell such as a TIL. The construction of multivalent vectors such as pox viral vectors capable of delivering multiple genes is within the level of skill in the art and may be effected by known methodologies. The co-expression of a lymphokine such as GM-CSF and an antigenic polypeptide, such as a cancer antigen, by a poxviral vector ensures that they are produced together by the same target host cells in a very localized area. Such expression has been shown to significantly enhance the immunological response to the cancer antigens (Tao, et al. *Nature*, 362:755 (1993)).

The vector can also be used to deliver genes to enhance the ability of the immune system to fight a particular disease or tumor. For example, a vector delivering one or more cytokines (e.g., IL-2) to boost the immune system and/or one or more an antigens.

Other cancer therapy approaches suitable for use with the method of the present invention include introduction of tumor suppressor genes (e.g., retinoblastoma gene) into tumor cells (T. Friedmann, *Cancer,* 70:1810 (1992)), inhibition of expression of oncogenes (e.g., ras, neu) in tumor cells (T. Mukhopadhyay, et al., *Cancer Res.,* 51:1744 (1991)), rendering bone marrow cells resistant to the toxic effects of chemotherapy (S. Podda, et al., *Proc. Natl. Acad. Sci. USA,* 89:9676 (1992); S. P. Sorrentino, et al., *Science,* 257:99 (1992)), and introduction of conditionally toxic genes into tumor cells (M. P. Short, et al., *Neurosci. Res.,* 27:427 (1990); K. N. Culver, et al., *Science,* 256:1550 (1992)).

The first use of genetic therapy in humans involved tumor infiltrating lymphocytes (TILs) as target cells (see, Rosenberg, et al., *New Engl. J. Med.,* 9:570–578 (1990)). TILs are a lymphocyte subpopulation that show promise as vehicles for delivery of anti-cancer therapeutics to tumor sites. These lymphocytes infiltrate into tumors, as part of an attempt by the host's immune system to mount an immunological response.

TIL cells for use as target host cells for gene delivery can be produced in vitro by incubating resected human tumors, such as kidney, colon or breast tumors, melanomas, and sarcomas in vitro in appropriate tissue culture medium that contains interleukin-2 (IL-2). The IL-2 in the medium results in the expansion and activation of T cells within the tumor, the TIL cells, and the destruction of tumor cells or tissue. After 2–8 weeks in culture, the tumor cells have been destroyed and the culture primarily contains lymphcid cells that have the phenotype of cytolytic T lymphocytes (CTL) (see, e.g., Rosenberg, et al., *New Engl. J. Med.,* 319:1676–1680 (1988); Muul, et al., *J. Immunol.,* 138:989–995 (1987); and Topalian, et al., *J. Immunol.,* 142:3714–3725 (1987)).

Generally, between $1 \times 10^5$ and a maximum of $2 \times 10^{11}$ cells per infusion are administered in, for example, one to three infusions of 200 to 250 ml each over a period of 30 to 60 minutes. After the completion of the infusions, the patient may be treated with recombinant interleukin-2 with a dose of 720,000 IU per kilogram of body weight intravenously every eight hours; some doses can be omitted depending on the patient's tolerance for the drug.

TILs can also be modified by introduction of a viral vector containing a DNA encoding TNF and reintroduced into a host in an effort to enhance the anti-tumor activity of the TIL cells. Other cytokines can also be used.

TIL cells also show promise for use in methods of genetic therapy, particularly cancer therapy, (see, e.g., Culliton, "News and Comment" in *Science,* 244:1430–1433 (1989) and Kasid, et al., *Proc. Natl. Acad. Sci.,* 87:473–477 (1990)) because they provide a source of autologous cells that target tumors and that can be modified by the insertions of DNA encoding a desired protein, cultured, and reintroduced into the patient.

The method of the present invention may be used to deliver genes encoding, for example, TNF and/or interleukin-2 (IL-2) to tumor cells. It is expected that secretion of these cytokines will stimulate a tumor-specific immune response that would either result in tumor destruction at other sites or allow the collection of more effective TIL from lymph nodes near the site of the injected tumor cells.

Introduction of the viral vector carrying the gene to be delivered to the target host cell may be effected by any method known to those of skill in the art.

One would inject a sufficient amount of the viral vectors to obtain a serum concentration in the organ of interest of the protein ranging between about 1 pg/ml to 20 µg/ml. More preferably between about 0.1 µg/ml to 10 µg/ml. Still more preferably, between about 0.5 µg/ml to 10 µg/ml.

The effect of the genetic material delivered can be carefully monitored and regulated using this system. Preferred vectors such as swinepox will only express the genetic material for about two weeks. Thus, if the condition being treated is alleviated within that time frame, since the vector system is self limiting no unnecessary material will be produced after that time period. Where additional dosages will be needed, additional administration of the material can be accomplished by repeating the injection. In certain cases, the addition of a second, third, etc. material can also be added with these vectors.

The present invention is further illustrated by the following Examples. These Examples are provided to aid in the understanding of the invention and are not construed as a limitation thereof.

REFERENCE EXAMPLE 1

CONSTRUCTION OF NON-LYTIC, NON-CYTOPATHIC VECTORS

Parent Viruses

A number of viruses, including retroviruses, adenoviruses, herpes viruses, and pox viruses, have been developed as live viral vectors for the expression of heterologous proteins (Cepko et al., Cell 37:1053–1062 (1984); Morin et al., Proc. Natl. Acad. Sci. USA 84:4626–4630 (1987); Lowe et al., Proc. Natl. Acad. Sci. USA, 84:3896–3900 (1987); Panicali & Paoletti, Proc. Natl. Acad. Sci. USA, 79:4927–4931 (1982); Machett et al., Proc. Natl. Acad. Sci. USA, 79:7415–7419 (1982)). Viruses meeting the above definition of non-lytic, non-cytopathic can ready be selected for use as the parent virus. Representative fowlpox and swinepox virus are available through the ATCC under accession numbers VR-229 and VR-363, respectively.

DNA Vectors For In Vivo Recombination With A Parent Virus

Genes that code for desired polypeptides are inserted into the genome of a parent virus in such a manner as to allow them to be expressed by that virus along with the expression of the normal complement of parent virus proteins. This can be accomplished by first constructing a DNA donor vector for in vivo recombination with a parent virus.

In general, the DNA donor vector contains the following elements:

(i) a prokaryotic origin of replication, so that the vector may be amplified in a prokaryotic host;

(ii) a gene encoding a marker which allows selection of prokaryotic host cells that contain the vector (e.g., a gene encoding antibiotic resistance);

(iii) at least one gene encoding a desired protein located adjacent to a transcriptional promoter capable of directing the expression of the gene; and (iv) DNA sequences homologous to the region of the parent virus genome where the foreign gene(s) will be inserted, flanking the construct of element (iii).

Methods for constructing donor plasmids for the introduction of multiple foreign genes into pox virus are described in WO91/19803, the techniques of which are incorporated herein by reference. In general, all DNA fragments for construction of the donor vector, including fragments containing transcriptional promoters and fragments containing sequences homologous to the region of the parent virus genome into which foreign genes are to be inserted, can be obtained from genomic DNA or cloned DNA fragments. The donor plasmids can be mono-di-, or multivalent (i.e., can contain one or more inserted foreign gene sequences).

The donor vector preferably contains an additional gene which encodes a marker which will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., J. Virol., 62:1046 (1988); Falkner and Moss., J. Virol., 62:1849 (1988); Franke et al., Mol. Cell. Biol., 5:1918 (1985), as well as genes such as the E. coli lacZ gene, that permit identification of recombinant viral plaques by calorimetric assay (Panicali et al., Gene, 47:193–199 (1986)).

Integration Of Foreign DNA Sequences Into The Viral Genome And Isolation Of Recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603, 112, WO89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK and can be selected on this basis (Mackett et al., Proc. Natl. Acad. Sci. USA, 79:7415 (1982)). Alternatively, co-integration of a gene encoding a marker or indicator gene with the foreign gene(s) of interest, as described above, can be used to identify recombinant progeny. One preferred indicator gene is the E. coli lacZ gene: recombinant viruses expressing β-galactosidase can be selected using a chromogenic substrate for the enzyme (Panicali et al., Gene, 47:193 (1986)).

Following in vivo recombination, recombinant viral progeny can be identified by one of several techniques. The presence of integrated foreign DNA can be detected by hybridization with a labeled DNA probe specific for the inserted DNA. Preferred techniques for selection, however, are based upon co-integration of a gene encoding a marker or indicator gene along with the gene of interest, as described above, A preferred indicator gene is the E. coli lacZ gene which encodes the enzyme β-galactosidase. Selection of recombinant virus expressing β-galactosidase can be done by employing a chromogenic substrate for the enzyme. For example, recombinant viruses are detected as blue plaques in the presence of the substrate 5-bromo-4-chloro-3-indolyl-β-D-galactosidase or other halogenated-indolyl-β-D-galactosidase (e.g., BluGal™).

Characterizing The Viral Antigens Expressed By Recombinant Viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA).

REFERENCE EXAMPLE 2

SELECTION OF NON-LYTIC, NON-CYTOPATHIC VECTORS

The parental recombinant virus is selected, thereafter one determines an insertion site. This can be by a variety of techniques including use of a known site, a determination of a site in the parent virus that is not essential, with pox virus one typically can use the TK gene. A desired gene, preferably a marker gene such as β-gal, is inserted into the insertion site. The viral vector is then introduced into a target TIL cell by standard techniques. The expression of the marker is then measured to determine the appropriateness of the vector for the host.

EXAMPLE 1

CONSTRUCTION OF VECTORS

The ability of a vector to transform a target host can readily be determined by the use of a marker gene such as β-galactosidase, CAT, etc. The marker permits the ready identification and quantification of a vector's interaction with a particular host cell to determine its suitability for transferring a desired gene. Other than ease of detection, there is no difference in the expression of a marker gene or another gene.

Recombinant fowlpox viruses (FPV) were constructed by homologous recombination in a manner analogous to that previously described (Jenkins, et al. *AIDS Research and Human Retroviruses* 7:991–998 (1991). Foreign sequences were inserted at the Bg/II site in the BamHI J region of the FPV genome. FPV 12-I was constructed using plasmid vector pAbT2300 and contains the *E. coli* lacZ gene under the control of the vaccinia 40K promoter (designated H6 in Rosel, et al. *J. Virol.* 60:436–439 (1986)). FPV 66, 67, 72 and 75 were constructed using plasmid vectors pAbT4125, pAbT4123, pAbT4132 and pAbT859, respectively. Each contain the lacZ gene under the control of the FPV C1 promoter (Jenkins, et al., supra (1991)); these four recombinants each contain one additional gene, namely the $HIV_{IIIB}$env gene, the $SIV_{mac251}$env gene, an *Eimeria tenella* gene, or the $HIV_{IIIB}$gag-pol gene, respectively, each under the control of the 40K promoter. vT32 was constructed using plasmid vector pAbT1016 and contains the gene encoding the cytokine tumor necrosis factor under the control of the vaccinia 40K promoter and the lacZ gene under the control of the FPV C1 promoter.

Recombinant swinepox viruses (SPV) were constructed by homologous recombination in a manner analogous to that previously described (Mackett, et al., *Proc. Natl. Acad. Sci. USA* 79:7415–7419 (1982)). Foreign sequences were inserted at the NdeI site in the thymidine kinase region of the SPV genome (Feller, et al., supra (1991)). SPV v17a was constructed using plasmid vector pJAF: lacZ and contains the lacZ gene under the control of the vaccinia 11K promoter. SPV vT6R was constructed using plasmid vector pT105 and contains the HIV gag p55 gene (WO91/19803) under the control of the vaccinia 7.5K promoter and the lacZ gene under the control of the 11K promoter. The vaccinia/TNF and vaccinia/IL-2 recombinants were constructed using plasmid vector pT1021 and pT2004, respectively. Each contains the gene encoding the cytokine TNF or IL-2 under the control of the vaccinia 40K promoter and the lacZ gene under the control of the fowlpox C1 promoter.

A sample of plasmids pT1016 and pT105 were deposited under the terms of the Budapest Treaty with the American Type Culture Collection (ATCC), 12301 Parklawn Drive, Rockville, Md. U.S.A., on May 2, 1994 and received ATCC accession numbers 75765 and 75766, respectively.

EXAMPLE 2

INFECTIVITY, VIABILITY AND DURATION OF VECTOR-MEDIATED GENE EXPRESSION IN TUMOR-INFILTRATING LYMPHOCYTES AND HUMAN LYMPHOCYTE CELL LINES INFECTED WITH RECOMBINANT FPV OR SPV

For each multiplicity of infection, TIL cells were suspended in a mixture of buffer+virus to give the desired multiplicity. After incubation at 37° C. for 15 min., cells were diluted in AIM V culture medium containing IL-2 and antibiotics. Cells were then plated in multiwell tissue culture plates, with each well receiving $10^6$ cells. Cells were incubated at 37° C. for various times. At each time point, two wells at each multiplicity were independently harvested, counted for total viable cells by staining with trypan blue, then fixed with glutaraldehyde and stained with X-gal to detect cells expressing β-galactosidase. The results of the Experiments are set forth below.

Experiment 1 (Human TIL+FPV 12-I)

| | Time post infection (hours) | | | | | | | |
|---|---|---|---|---|---|---|---|---|
| | 5 | | 24 | | 48 | | 96 | |
| MOI | cells/well | % lacZ⁺ | cells/well | % lacZ⁺ | cells/well | % lacZ⁺ | cells/well | % lacZ⁺ |
| 0 | $8.0 \times 10^5$ | 0 | $9.6 \times 10^5$ | 0 | $1.6 \times 10^6$ | 0 | $2.2 \times 10^6$ | 0 |
| 2 | $6.7 \times 10^5$ | 24.5 | $9.3 \times 10^5$ | 14.5 | $2.5 \times 10^6$ | 9.5 | $6.1 \times 10^6$ | 9.0 |
| 10 | $8.1 \times 10^5$ | 77.5 | $7.4 \times 10^5$ | 84.0 | $1.8 \times 10^8$ | 85.5 | $5.0 \times 10^6$ | 81.5 |

Experiment 2 (Human TIL+FPV 12-I)

| | Time post infection (days) | | | | | | | | | | | |
|---|---|---|---|---|---|---|---|---|---|---|---|---|
| | 1 | | 2 | | 3 | | 4* | | 6 | | 7** | |
| MOI | cells/well | % lacZ⁺ | cells/well | % lacZ⁺ | cells/well | % lacZ⁺ | cells/well | % lacZ⁺ | cells/well | % lacZ⁺ | cells/well | % lacZ⁺ |
| 0 | $1.2 \times 10^5$ | 0 | $2.3 \times 10^6$ | 0 | $2.1 \times 10^6$ | 0 | $3.6 \times 10^6$ | 0 | $4.0 \times 10^5$ | 0 | $1.8 \times 10^6$ | 0 |
| 2 | $1.4 \times 10^6$ | 39 | $1.7 \times 10^6$ | 33 | $3.6 \times 10^6$ | 14.5 | $4.5 \times 10^6$ | ND | $5.3 \times 10^6$ | 10.5 | $1.1 \times 10^6$ | 6.5 |
| 10 | $1.0 \times 10^6$ | 95 | $1.3 \times 10^6$ | 97.5 | $2.4 \times 10^6$ | 61 | $4.8 \times 10^6$ | ND | $3.6 \times 10^6$ | 94.5 | $1.3 \times 10^6$ | 100 |

-continued

| | Time post infection (days) | | | | | | | | | | | |
|---|---|---|---|---|---|---|---|---|---|---|---|---|
| | 1 | | 2 | | 3 | | 4* | | 6 | | 7** | |
| MOI | cells/well | % lacZ+ | cells/well | % lacZ+ | cells/well | % lacZ+ | cells/well | % lacZ+ | cells/well | % lacZ+ | cells/well | % lacZ+ |
| 30 | $1.1 \times 10^6$ | 100 | $1.3 \times 10^6$ | 100 | $2.1 \times 10^6$ | 34.5 | $4.4 \times 10^6$ | ND | $4.1 \times 10^6$ | 100 | $1.6 \times 10^6$ | 98 |

*Cells were split to $4 \times 10^5$ cells/well on day 4
**Cultures were contaminated by day 6

Experiment 3 (Mouse MC-38 TIL+FPV 12-I)

| | Time post infection (days) | | | | | | | |
|---|---|---|---|---|---|---|---|---|
| | 1* | | 4 | | 5 | | 7** | |
| MOI | cells/well | % lacZ+ | cells/well | % lacZ+ | cells/well | % lacZ+ | cells/well | % lacZ+ |
| 0 | $2.1 \times 10^6$ | 0 | $5.4 \times 10^5$ | 0 | $5.9 \times 10^6$ | 0 | $3.0 \times 10^6$ | ND*** |
| 2 | $1.1 \times 10^6$ | 30.5 | $8.4 \times 10^5$ | 15 | $5.9 \times 10^6$ | 15.5 | $2.1 \times 10^6$ | ND |
| 10 | $2.1 \times 10^6$ | 95 | $4.1 \times 10^5$ | 25 | $3.3 \times 10^6$ | 23 | $2.0 \times 10^6$ | ND |

*Cells were split to $2.5 \times 10^5$ cells/well on day 1
**Cultures were contaminated by day 5
***ND = Not Done Experiment 4 (Human TIL+SPV v17a)

TABLE A

| | Time post infection (days) | | | | | | | | | |
|---|---|---|---|---|---|---|---|---|---|---|
| | 1 | | 2 | | 3* | | 4 | | 7 | |
| MOI | cells/well | % lacZ+ | cells/well | % lacZ+ | cells/well | % lacZ+ | cells/well | % lacZ+ | cells/well | % lacZ+ |
| 0 | $9.5 \times 10^5$ | 0 | $2.0 \times 10^6$ | 0 | $1.9 \times 10^6$ | ND | $4.0 \times 10^6$ | 0 | $6.7 \times 10^6$ | 0 |
| 2 | $1.1 \times 10^6$ | 76 | $1.6 \times 10^6$ | 76 | $3.8 \times 10^6$ | ND | $3.8 \times 10^6$ | 32 | $1.5 \times 10^7$ | 6.5 |
| 10 | $7.0 \times 10^5$ | 100 | $5.0 \times 10^6$ | 100 | $1.0 \times 10^6$ | ND | ND | ND | ND | ND |

*Cells were split to $10^6$ cells/well on day 3

TABLE B

| | % viable cells after | | | | | |
|---|---|---|---|---|---|---|
| MOI | 5 hours | 1 day | 2 days | 3 days* | 4 days | 7 days |
| 0 | 89.5 | 80 | 89 | 96 | 93 | 90.5 |
| 2 | 89.5 | 91 | 94.5 | 94 | 87.5 | 90.5 |
| 10 | 87 | 58 | 54 | 62 | ND | 0 |

*Cells were split to $10^6$ cells/well on day 3

EXAMPLE 3

RECOMBINANT FPV-DIRECTED EXPRESSION OF FOREIGN PROTEINS IN HUMAN LYMPHOCYTES

Cells were infected at the indicated MOI and expression of the foreign protein was assayed 24 hours post-infection. For assay of envelope glycoprotein expression, cells were observed microscopically for the presence of syncytia. For assay of lacZ expression, single cell blue analysis was performed. Expression was analyzed 24 hours post-infection. In all experiments, the negative control was wild type FPV.

| Experiment No. | Cell line[1] | Virus | Foreign Gene Assayed | MOI[2] | Result |
|---|---|---|---|---|---|
| 1 | SUP-T1 | FP66 | HIV env | 20 | No syncytia |
| | | FP67 | SIV env | ND[3] | + syncytia |
| 2 | HUT-78 | FP66 | HIV env | 20 | No syncytia |
| 3 | SUP-T1 | FP66 | HIV env | 50 | + syncytia |
| | | FP67 | SIV env | 50 | + syncytia |
| | HUT-78 | FP66 | HIV env | 50 | No syncytia |
| | | FP67 | SIV env | 50 | No syncytia |
| 4 | JY-LCL | FP72 | E. coli LacZ | 1 | 5–10% LacZ+ |
| | | | | 10 | 5–10% LacZ+ |
| | | | | 100 | 5–10% LacZ+ |
| 5 | JY-LCL | FP72 | E. coli LacZ | 1 | 10% LacZ+ |
| | | | | 10 | 10% LacZ+ |
| | | | | 100 | 50–60% LacZ+ |
| 6 | JY-LCL | FP72 | E. coli LacZ | 10 | 10% LacZ+ |
| | | | | 25 | 10–15% LacZ+ |
| | | | | 50 | 60–70% LacZ+ |
| | | | | 100 | 70–80% LacZ+ |

-continued

| Experiment No. | Cell line[1] | Virus | Foreign Gene Assayed | MOI[2] | Result |
|---|---|---|---|---|---|
| 7 | JY-LCL | FP66 | E. coli LacZ | 50 | 50–60% LacZ+ |
|   |        | FP75 | E. coli LacZ | 50 | 50–60% LacZ+ |

[1]SUP-T1 and HUT-78 are human T cell lines that express CD4; JY-LCL is a human B cell line.
[2]MOI: Multiplicity of infection
[3]ND: Not determined. An untitered stock of virus was used

EXAMPLE 4

TIL cells infected with 12-I (FPV/lacZ) at varying multiplicities of infection (MOI=2, 5, or 20 pfu/cell) were analyzed using a fluorescence activated cell sorter on days 1, 2, 3, 4 and 7 post infection. Comparison with a standard provides an indication of the number of cells expressing β-galactosidase. The data indicated that at higher MOI (5 and 20), β-galactosidase expression can be detected for three days at MOI=5 and at least 4 days at MOI=20. By day 7, no detectable expression remained at any MOI examined.

Using TIL cells from the same patient, the percent of cells transduced as a function of MOI and days after infection was determined. The percent of cells transduced remained low (15% at MOI=2, 33% at MOI=5) and peaked at two days at low and intermediate MOI. At a high MOI (MOI=20), transduction efficiency was high, reaching 99% at day two and remaining relatively high through day 4 (44%). The percent of transduced cells returned to background levels by day 7. During the same time period, the cells infected with FPV/lacZ continued to grow normally as compared to uninfected controls.

Comparison of 12-I (FPV/lacZ) and v17a (SPV/lacZ) expression in TIL cells for a different patient showed no significant difference between level of transduction or duration of expression between the two vectors. Cell growth was unaffected by infection with either vector.

A recombinant FPV vT32 expressing both lacZ and TNF was compared with FPV 12-I, a vector expressing lacZ alone. Both recombinants infected significant percentages of cells at high MOI compared to low MOI or controls. Expression of β-galactosidase by either 12-I or vT32 remained at initial values for at least 3 days and, for 12-I, the single gene insert, as long as 7 days post infection. Cell growth remained normal during the course of the experiment.

EXAMPLE 5

INFECTIVITY, GENE EXPRESSION, AND CYTOPATHIC EFFECT IN VARIOUS CELL LINES INFECTED WITH SPV

To investigate the ability of swinepox virus (SPV) to infect and undergo gene expression in cells derived from various species, gene expression was assessed in infected porcine (PK-15), rabbit (RK-13), and primate (VERO and BSC40) cells. Cells were infected with an SPV recombinant, v17a, containing the lacZ gene at an MOI of 5 or 1 pfu/cell. Twenty-four hours later, cells were observed microscopically with respect to cytopathic effect (CPE) and were stained with Xgal to observe expression of the SPV-encoded lacZ gene. The percentage of blue cells was determined, indicating infection with SPV and expression of β-galactosidase. The results are shown in Table (1).

TABLE (1)

| Cell line | MOI = 5 | | MOI = 1 | |
|---|---|---|---|---|
|  | Blue Cells (%) | CPE (%) | Blue Cells (%) | CPE (%) |
| PK-15 | 7.5 | 0 | 1.5 | 0 |
| RK-13 | 5.0 | 100 | 1.0 | 100 |
| BSC-40 | 100.0 | 0 | 100.0 | 0 |
| VERO | 24.0 | 0 | 5.0 | 0 |

The results demonstrate that SPV can infect BSC-40 cells without causing cytopathic effect (CPE) and can express β-galactosidase in these cells.

EXAMPLE 6

LOW REPLICATIVE EFFICIENCY OF SPV

To examine the replicative efficiency of SPV, 6 cm plates of BSC-40 and PK-15 cells, each containing approximately $10^6$ cells, were infected with SPV at an MOI of 0.1 or 0.01 pfu/cell. Virus was harvested 5 days post-infection and titered on PK-15 cells. The results are shown below in Table (2).

TABLE (2)

| MOI (pfu/cell) | Input virus (pfu) | Virus yield (pfu) on: | | pfu/cell on: | |
|---|---|---|---|---|---|
|  |  | BSC-40 cells | PK-15 cells | BSC-40 cells | PK-15 cells |
| 0.01 | $10^4$ | $5.87 \times 10^5$ | $1.56 \times 10^7$ | 0.59 | 15.6 |
| 0.10 | $10^5$ | $7.50 \times 10^5$ | $1.80 \times 10^7$ | 0.75 | 18.0 |

These results indicate that SPV has a replicative efficacy of approximately 0.7 pfu/cell on BSC-40 cells and 17 pfu/cell on PK-15 cells.

EXAMPLE 7

DURATION OF SPV-MEDIATED PROTEIN EXPRESSION BY INFECTED CELLS

To assess the ability of recombinant SPV to direct protein expression in non-porcine cells, BSC-40 cells were infected with a recombinant SPV v17a, that contains the E. coli lacZ gene, and lacZ expression was evaluated by Western blot using a monoclonal antibody against β-galactosidase. BSC-40 cells were infected at an MOI of 1 or 0.1 pfu/cell with a SPV recombinant containing the lacZ gene and cell lysates were prepared 2, 3 and 4 days post-infection. Western analysis was performed using a monoclonal antibody specific for β-galactosidase. β-galactosidase expression was detected in all samples.

Similar expression analysis was then performed using SPV recombinant vT6R, which expresses the HIV gag p55 precursor polypeptide. BSC-40 and PK-15 cells were infected an MOI of 0.1 pfu/cell. Media were removed 2 days post-infection and centrifuged at high speed to pellet any HIV-like particles present, and cells were replenished with DME+5% FCS. Two days later, media were again harvested and fractionated by high speed centrifugation, and the infected cells were lysed in hypotonic solution containing PMSF. Western blot analysis was performed using human HIV+antiserum. This experiment showed that both the cell lysates and the material pelleted after high speed centrifugation of the culture media contain the p55 gag precursor polypeptide. These experiments suggest that SPV-mediated gene expression continues in infected cells for at least 4 days.

Subsequent experiments were designed to examine the duration of SPV-mediated gene expression in 3 different cell lines. In these experiments, various cell culture parameters, such as serum concentration, re-feeding of cells, and multiple media harvests were evaluated. Cells were infected with vT6R at an MOI of 0.1 pfu/cell and cell lysates and culture media were processed as described above. The experiment continued until infected cells showed high CPE. The experimental protocol is outlined in Table (3).

TABLE (3)

| Cell Line | Input pfu | Culture Medium | % FCS | Harvest |
|---|---|---|---|---|
| PK-15 | $1.7 \times 10^6$ | DME | 5 | multiple harvest |
|  |  | DME | 2 | multiple harvest |
|  |  | DME | 5 | no harvest |
|  |  | ExCell 30× | 2 | no harvest |
| BSC-40 | $2.0 \times 10^6$ | DME | 1 | multiple harvest |
|  |  | DME | 2 | no harvest |
| RK-13 | $2.0 \times 10^6$ | DME | 1 | multiple harvest |
|  |  | DME | 2 | no harvest |

Particle preparations were analyzed by Western blot using the p24-specific monoclonal antibody and were titered for the presence of SPV. In addition, some of the preparations were assayed by p24 ELISA. The results indicated that PK-15 and BSC-40 cell lines produced the maximum amount of HIV-1 gag p55 particles and RK-13 cells produced less. Gene expression was observed for six to seven days, until high CPE was observed. SPV titers decreased after removing the media (which removes residual input virus) and re-feeding infected monolayers indicating low replicative efficacy.

The experiment was repeated using BSC-40 cells, infected with vT6R at an MOI of 0.1 pfu/cell in media containing varying amount of serum. The viral inoculum was removed 24 hours post-infection, and monolayers were washed twice with DME containing varying amounts of serum. Multiple harvesting and re-feeding were performed. Particle preparations were prepared and subjected to Western blot analysis, SPV titration, and p24 ELISA. The results confirmed good levels of HIV-like particle production for six days. In addition, low titers of SPV were obtained indicating low replicative efficacy.

EXAMPLE 8

VIABILITY AND DURATION OF VECTOR-MEDIATED GENE EXPRESSION IN TUMOR-INFILTRATING LYMPHOCYTES (TILs) INFECTED WITH RECOMBINANT FOWLPOX VIRUS (FPV)

Human TIL cells, patient number 1306, were infected with a recombinant fowlpox virus 12-I, containing the lacZ gene, at a multiplicity of infection (MOI) of 10. Infected cells were stained with Xgal at various times post-infection and were examined microscopically to determine the percentage of blue cells present, indicating infection with FPV and expression of β-galactosidase. In addition, cells were stained with trypan blue to determine the percentage of viable cells at various times post-infection. To allow cells to continue to grow, cells were split at days 3 and 8 by harvesting and replating cells at a subconfluent density. Duplicate samples were analyzed. The results are shown in Table (4).

TABLE (4)

| Viability and LacZ Expression in FPV/lacZ-Infected TIL Cells | | | | | | | |
|---|---|---|---|---|---|---|---|
| | Viability (%) | | | | LacZ Expression (%) | | |
| | MOI = 0 | | MOI = 10 | | MOI = 0 | | MOI = 10 | |
| DAY | Sample 1 | Sample 2 | Sample 1 | Sample 2 | Sample 1 | Sample 2 | Sample 1 | Sample 2 |
| 1 | 98 | 97 | 97 | 95 | 0 | 0 | 100 | 100 |
| 2 | 97 | 100 | 91 | 90 | 0 | 0 | 100 | 100 |
| 4 | 98 | 100 | 95 | 94 | 0 | 0 | 100 | 100 |
| 7 | 96 | 98 | 97 | 97 | 0 | 0 | 100 | 100 |
| 9 | 81 | 82 | 94 | 95 | 0 | 0 | 100 | 100 |

The results indicate that FPV can infect human TILs and express β-galactosidase for at least 9 days. In addition, a high level of cell viability is maintained in the infected cells.

In another experiment, four different human TIL cells (patient numbers 1394, 1395, 1362 and 1359) were infected, at various MOIs, with vT32, a fowlpox recombinant expressing the cytokine tumor necrosis factor (TNF). TNF is normally expressed and secreted into the culture medium of infected cells. Culture media were collected at various times over a four day infection period and were assayed for TNF by ELISA (Quantikine Kit, R&D Systems). Cell viability was also monitored during this time period. Results are shown in Tables (5) and (6).

TABLE (5)

| Viability of FPV/TNF-Infected TIL Cells (%) | | | | | | |
|---|---|---|---|---|---|---|
| | Day 2 | | | Day 3 | | |
| TIL Cells | MOI = 0 | MOI = 30 | MOI = 100 | MOI = 0 | MOI = 30 | MOI = 100 |
| 1394 | 88 | 86 | 72 | 96 | 92 | 90 |
| 1395 | 93 | 87 | 91 | 96 | 92 | 90 |

TABLE (5)-continued

Viability of FPV/TNF-Infected TIL Cells (%)

| | Day 2 | | | Day 3 | | |
|---|---|---|---|---|---|---|
| TIL Cells | MOI = 0 | MOI = 30 | MOI = 100 | MOI = 0 | MOI = 30 | MOI = 100 |
| 1362 | 98 | 96 | 92 | 95 | 97 | 95 |
| 1359 | 92 | 93 | 89 | 96 | 96 | 96 |

TABLE (6)

TNF Expression in FPV/TNF-Infected TIL Cells

| | Day 2–3 | | | Day 3–4 | | |
|---|---|---|---|---|---|---|
| TIL Cells | MOI = 0 | MOI = 30 | MOI = 100 | MOI = 0 | MOI = 30 | MOI = 100 |
| 1394 | ND* | ND | ND | 4.3 | 9970 | 283 |
| 1395 | 4.8** | 2002 | 485 | 3.8 | 3840 | 4950 |
| 1362 | 8.5 | 3100 | 4050 | 16.2 | 2350 | 6420 |
| 1359 | 1 | 133 | 1460 | 13.8 | 394 | 8960 |

*ND = not determined;
**TNF levels are expressed as picograms TNF/$5 \times 10^5$ cells/ml/24 hrs Uninfected TILs show a low background level of TNF reactivity in this assay. However, TNF levels are much higher in cells infected with fowlpox recombinant containing TNF. The results in Tables (4)–(6) indicate that recombinant fowlpox can infect a variety of TIL cells and can maintain a high level of cell viability and vector-mediated gene expression.

EXAMPLE 9

VIABILITY AND DURATION OF VECTOR-MEDIATED GENE EXPRESSION IN HUMAN TUMOR CELL LINES INFECTED WITH RECOMBINANT FOWLPOX VIRUS

Human TIL cells (patient number 1327) and a human melanoma tumor cell line (patient number 1143) were infected at a variety of MOIs with recombinant FPV, FPV 12-I, containing the lacZ gene. Viability and β-galactosidase expression were monitored at day 1 and day 5 post-infection. Duplicate samples were analyzed. The results are shown in Table (7).

The results indicate high infectivity and expression of the FPV-encoded lacZ gene in both 1327 TIL cells and the human melanoma cell line 1143 infected with recombinant FPV. The viability of uninfected melanoma cells was more variable than that of TILs, but infection with recombinant FPV did not alter the viability of the cells for the 5-day duration of this experiment.

Viability and FPV-mediated gene expression were assessed on two additional tumor cell lines (melanoma patient number 1182 and melanoma patient number 1199) infected with recombinant FPV containing the TNF gene or the lacZ gene. Cells were infected at MOIs of 0 and 20 and were monitored for three days post-infection. Cell viability was assessed and TNF levels in the culture media from infected cells were measured by ELISA. The results are shown in Table (8).

TABLE (8)

Viability and TNF Expression in FPV/TNF-Infected Tumor Cell Lines

| Tumor Cells | Foreign Gene | MOI | Viability (%) | | | TNF Expression (pg/$10^5$ cells/ml/24 hrs) | |
|---|---|---|---|---|---|---|---|
| | | | Day 1 | Day 2 | Day 3 | Day 1–2 | Day 2–3 |
| 1182 | — | 0 | 90 | 95 | 92 | ND* | ND |
| 1182 | lacZ | 20 | 92 | 100 | 89 | 0 | 41.2 |
| 1182 | TNF | 20 | 82 | 92 | 89 | 83700 | 549800 |
| 1199 | — | 0 | 91 | 88 | 82 | ND | ND |
| 1199 | lacZ | 20 | 76 | 75 | 37 | 1.6 | 0 |
| 1199 | TNF | 20 | 91 | 79 | 81 | 35900 | 31650 |

*ND = Not done.

High levels of vector-mediated expression of TNF in human tumor cell lines infected with recombinant FPV were observed over the 3-day duration of this experiment.

EXAMPLE 10

DURATION OF VECTOR-MEDIATED GENE EXPRESSION IN FRESH HUMAN TUMOR CELLS INFECTED WITH RECOMBINANT FOWLPOX VIRUS

Tumor cells were extracted from melanoma tumors from three different patients (1376, 1360, and 1394). Cells were infected with vT32 at an MOI of 0 or 50, and TNF production was assessed by ELISA on the culture media

TABLE (7)

Viability and LacZ Expression in FPV/lacZ-Infected TIL and Tumor Cells

| | | Viability (%) | | | | LacZ Expression (%) | | | |
|---|---|---|---|---|---|---|---|---|---|
| | | MOI = 0 | | MOI = 10 | | MOI = 0 | | MOI = 10 | |
| Cells | DAY | Sample 1 | Sample 2 | Sample 1 | Sample 2 | Sample 1 | Sample 2 | Sample 1 | Sample 2 |
| TIL | 1 | 85 | 82 | 88 | 90 | 0 | 0 | 95 | 100 |
| TIL | 5 | 90 | 91 | 98 | 97 | 0 | 0 | 95 | 98 |
| Tumor | 1 | 73 | 100 | 70 | 75 | 0 | 0 | 100 | 100 |
| Tumor | 5 | 62 | 48 | 57 | 57 | 0 | 0 | 100 | 100 | taken various times post-infection. Results are shown in Table (9).

TABLE (9)

TNF Expression in FPV/TNF-Infected Fresh Tumor Cells

| Tumor Cells | MOI | TNF Expression (pg/$10^6$ cells/ml/24 hrs) | |
|---|---|---|---|
| | | Day 0–1 | Day 1–2 |
| 1376 | 0 | 0 | 300 |
| 1376 | 50 | 6167 | 36550 |
| 1360 | 0 | 106 | 36 |
| 1360 | 50 | 4053 | 28371 |
| 1398 | 0 | 381 | 81 |
| 1398 | 50 | 6750 | 51938 |

EXAMPLE 11

DURATION OF VECTOR-MEDIATED GENE EXPRESSION IN TIL CELLS INFECTED WITH ATTENUATED VACCINIA VIRUS

Vaccinia virus is normally cytopathic to cells, killing them rapidly. A recombinant vaccinia virus was constructed by inserting the TNF gene into the New York City Board of Health strain of vaccinia virus. TIL cells, patient number 1395, were infected with this virus at a variety of MOI. Cell viability was assessed at various times post-infection. The results are shown in Table (10).

TABLE (10)

Viability of TIL cells infected with non-attenuated vaccinia virus

| MOI | VIABILITY (%) | | |
|---|---|---|---|
| | DAY 1 | DAY 2 | DAY 3 |
| 0 | 93 | 91 | 94 |
| 2 | 85 | 15 | 12 |
| 10 | 82 | 20 | 17 |
| 30 | 77 | 27 | 20 |

An attenuated strains of vaccinia virus may achieve longer duration of infection and gene expression than "normal" strains of vaccinia, and thus may be candidate vectors for short-term gene therapy. The Wyeth Smallpox Vaccine strain of vaccinia virus is more attenuated than other strains of vaccinia virus. Furthermore, a virus stock derived from the Smallpox Vaccine by selecting and purifying an individual viral plaque is even more attenuted than the original Wyeth strain, as measured by neurovirulence in mice. This vaccinia virus is designated TBC-Wy.

The gene encoding human IL-2 was inserted into the HindIII M region of the genome of vaccinia strain TBC-Wy and was used to assess the duration of gene expression mediated by this attenuated, recombinant vaccinia virus in infected TIL cells. The White strain of TIL cells was infected with this recombinant, designated VT2004, at a variety of MOIs. IL-2 expression was measured by ELISA (Quantikine Kit, R&D Systems) after harvesting the culture media at various times post-infection. The results are shown in Table (11).

TABLE (11)

Viability and IL-2 Expression in Vaccinia/IL-2 Infected 1358 TIL Cells

| | Viability (%) | | | IL-2 Expression (pg/ml/5 × $10^5$ cells/24 hrs) | | |
|---|---|---|---|---|---|---|
| MOI | DAY 1 | DAY 2 | DAY 3 | DAY 0–1 | DAY 1–2 | DAY 2–3 |
| 0 | 98 | 92 | 97 | 0 | 35.6 | 187.7 |
| 3 | 95 | 90 | 91 | 283.1 | 462.9 | 1111.9 |
| 10 | 97 | 86 | 79 | 744.1 | 772.5 | 2169.2 |

Viability remains high in infected cells. Some background level of IL-2 is observed in uninfected cells, but infected cells show substantially higher levels of IL-2.

The TBC-Wy vaccinia/IL-2 recombinant was further tested in two additional TIL cells, patient numbers 1376 and 1381. TILs were infected at MOI 10 and 30, and culture media were harvested and tested for IL-2 by ELISA over a 4-day infection period. Cell viability is shown in Table (12) and IL-2 expression is shown in Table (13).

TABLE (12)

Vaccinia/IL-2-Infected TIL Cells: Viability

| TILs | MOI | Viability (%) | | |
|---|---|---|---|---|
| | | DAY 1 | DAY 2 | DAY 3 |
| 1376 | 0 | 94 | 96 | 100 |
| 1376 | 10 | 95 | 94 | 97 |
| 1376 | 30 | 91 | 91 | 94 |
| 1381 | 0 | 87 | 89 | 94 |
| 1381 | 0 | 93 | 95 | 78 |
| 1381 | 30 | 97 | 91 | 78 |

TABLE (13)

Vaccinia/IL-2-Infected TIL Cells: IL-2 Expression

| TILs | MOI | IL-2 Expression (pg/ml/5 × $10^5$ cells/24 hrs) | | |
|---|---|---|---|---|
| | | DAY 0–1 | DAY 1–2 | DAY 2–3 |
| 1376 | 10 | 690.4 | 185.4 | 65.0 |
| 1376 | 30 | 634.7 | 341.5 | 75.3 |
| 1381 | 10 | 1131.6 | 481.5 | 326.0 |
| 1381 | 30 | 1323.1 | 685.6 | 728.1 |

The results shown in Tables (11)–(13) indicate that TILs infected with attenuated vaccinia virus maintain a surprisingly high level of viability while expressing a high level of recombinant protein.

The references cited throughout the specification are incorporated herein by reference.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. A method of gene delivery and short term expression of an isolated nucleic acid segment in a target cell, wherein the target cell is used in somatic cell therapy or gene therapy which comprises introducing a non-integrative cytoplasmic viral vector into the target cell, wherein said non-integrative viral vector is derived from a virus that has a low replicative efficiency in the target cell and has at least one insertion site containing a heterologous gene operably linked to a promoter capable of expression in the host and wherein the short term expression is for a period of at least one week and less than two months and wherein said gene is expressed at detectable levels.

2. The method of claim 1, wherein the target cell is used in somatic cell therapy.

3. The method of claim 2, wherein the target cell is a tumor infiltrating lymphyocyte.

4. The method of claim 1, wherein the cytoplasmic virus is selected from the group consisting of pox viruses, iridoviruses, coronaviruses, togaviruses, caliciviruses and picornaviruses.

5. The method of claim 1, wherein the virus is a DNA virus.

6. The method of claim 4, wherein the pox virus is selected from the group of pox viruses consisting of suipox, avipox and capripox virus.

7. The method of claim 1, wherein the gene is selected from the group of genes encoding hormones, growth factors, enzymes, cytokines, receptors, and tumor suppressor genes.

8. The method of claim 3, wherein the predetermined tumor-infiltrating lymphocyte is from a mammal.

9. The method of claim 8, wherein the mammal is a primate, a domestic animal or a dog or cat.

10. The method of claim 1, wherein the non-integrative viral vector expresses more than one heterologous DNA segment.

11. The method of claim 1, wherein the vector is also non-lytic.

12. The method of claim 9, wherein the cytoplasmic virus is a DNA virus.

13. The method of claim 9, wherein the cytoplasmic virus is a pox virus.

14. The method of claim 13, wherein the pox virus is selected from the group of viruses consisting of swinepox, fowlpox, pigeon pox, and capripox.

15. A method for expressing a heterologous nucleic acid segment in a target cell for a period of between at least one week and two months or less, which comprises the steps of (a) selecting a heterologous gene to be expressed for said period of between at least one week and two months or less;

(b) selecting a non-integrative cytoplasmic viral vector derived from a virus that has a low replicative efficiency in the target cell and is capable of continuously expressing said heterologous gene for at least one week, wherein said vector has at least one insertion site for insertion of the heterologous nucleic acid segment operably linked to a promoter capable of expression in the target cells;

(c) inserting said heterologous DNA into the insertion site, and (d) introducing said vector into said target cell wherein said gene is expressed at detectable levels.

16. The method of claim 15, wherein the target cell is used in somatic cell therapy.

17. The method of claim 15, wherein the target cell is a tumor infiltrating lymphocyte.

18. The method of claim 15, wherein the pox virus is selected from the group of pox viruses consisting of suipox, avipox, capripox and orthopox virus.

19. The method of claim 18, wherein the orthopox virus is a strain that has been genetically modified or selected to be non-virulent in a host.

20. The method of claim 19, wherein the orthopox virus is vaccinia.

21. The method of claim 20, wherein the vaccinia is strain MVA and TBC-Wy.

22. The method of claim 18, wherein the pox virus is suipox, avipox and capripox.

23. The method of claim 22, wherein the avipox is fowlpox, canary pox and pigeon pox.

24. The method of claim 22, wherein the suipox is swinepox.

25. The method of claim 15, wherein the virus is a cytoplasmic virus selected from the group consisting of iridoviruses, coronaviruses, togaviruses, caliciviruses and picornaviruses.

26. A method of gene delivery and short term expression of a nucleic acid segment in cell, wherein the target cell is used in somatic cell therapy or gene therapy which comprises introducing a non-integrative viral vector into the target cell, wherein said non-integrative cytoplasmic viral vector is derived from a pox virus that has a low replicative efficiency in the target cell and has at least one insertion site containing a heterologous nucleic acid segment operably linked to a promoter capable of expression in the host and wherein the short term expression is for a period of at least one week and less than two months and wherein said gene is expressed at detectable levels.

* * * * *